(12) United States Patent
Feigelson et al.

(10) Patent No.: US 6,713,626 B2
(45) Date of Patent: Mar. 30, 2004

(54) PROCESS FOR SYNTHESIZING N-ARYL PIPERAZINES WITH CHIRAL N'-1-[BENZOYL(2-PYRIDYL)AMINO]-2-PROPANE SUBSTITUTION

(75) Inventors: Gregg Brian Feigelson, Monsey, NY (US); Joseph Zeldis, New City, NY (US); Ivo Jirkovsky, Waitsfield, VT (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/384,845

(22) Filed: Mar. 10, 2003

(65) Prior Publication Data

US 2003/0187265 A1 Oct. 2, 2003

Related U.S. Application Data

(60) Provisional application No. 60/363,431, filed on Mar. 12, 2002.

(51) Int. Cl.[7] .................... C07D 401/12; C07D 405/14
(52) U.S. Cl. ............................. 544/360; 544/364
(58) Field of Search .................. 544/360, 364

(56) References Cited

U.S. PATENT DOCUMENTS

5,424,313 A    6/1995   Hartog et al.
6,127,357 A  * 10/2000  Cliffe et al. ............ 514/210

FOREIGN PATENT DOCUMENTS

| JP | 01125357 A2 | 5/1989 |
|---|---|---|
| WO | WO 94/24115 | 10/1994 |
| WO | WO 95/33725 | 12/1995 |
| WO | 95/33743 | * 12/1995 |
| WO | 96/01656 | * 1/1996 |
| WO | 97/03982 | * 2/1997 |
| WO | WO 97/37655 | 10/1997 |
| WO | 02/44142 A2 | * 11/2001 |

OTHER PUBLICATIONS

Kagayaki Natsuka et al., J. Med. Chem., 1987, 1779–1787, 30.
Frank Kerrigan et al., Tetrahedron Letters, 1998, 2219–2222, 39.
Sheryl J. Hays, J. Labelled Compounds and Radiopharmaceuticals, 1986, 351, 24(4).
Jean–Louis Peglion et al., J. Med. Chem., 1995, 4044–4055, 38.
Shawn J. Stachel et al., Tetrahedron Letters, 1999, 5811–5812, 40.
Julian M.C. Golec et al., Bioorganic & Medicinal Chemistry Letters, 1997, 2181–2186, 7(17).
Dan Muller, J. Org. Chem., 1997, 411–416, 62.
G. Mark Taylor et al., Tetrahedron Letters, 1996, 1297–1300, 37(8).
Database Crossfire Beilstein, Reg. No. 3915193.
Database Crossfire Beilstein, Reg. No. 1512459.
Zoltan Zubovics, Eur. J. Med. Chem., 1986, 370–378, 21(5).
G. Cignarella et al., Il Farmaco—Ed. Sc., 1976, p. 194, 196, v. 31.
Lee T. Boulton, J. Chem. Soc., Perkins Trans. 1, 1999, 1421–1429.
G. Cignarella, Il Farmaco—Ed. Sc., 1976, 194–200, 31(3).
Ulrike Burkard et al., Chem. Ber., 1986, 1594–1612, 119.
Wincenty Kwapiszewski et al., Acat Pol. Pharm., 1999, 41–47, 56(1) (Abstract).
Michimasa Izumi et al., Chem. and Pharm. Bull. (Japan), 1954, 275–279, 2(3).
Isao Aiko et al., Chem. and Pharm. Bull. (Japan), 1957, 487–488, 5(5).
Syed M. Quadri et al., Bioorganic & Medicinal Chemistry Letters, 1992, 1661–1664, 2(12).
G. Mark Taylor et al., Tetrahedron Letters, 1996, 1297–1300, 37(8).
Robert V. Hoffman et al., Tetrahedron Letters, 1990, 2953–2956, 31(21).
Sandrine Marchais et al., Bioorganic & Medicinal Chemistry, 2001, 695–702, 9.

* cited by examiner

*Primary Examiner*—Emily Bernhardt
(74) *Attorney, Agent, or Firm*—Rebecca R. Barrett

(57) ABSTRACT

A process for formation of N-aryl piperazines with chiral N'-1-[benzoyl(2-pyridyl)amino]-2-propane side-chains having the structure shown in formula below, and for making intermediate compounds therefor.

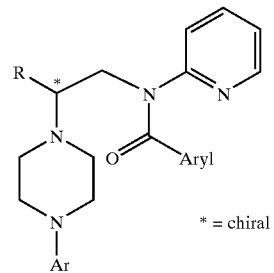

In this process, chirality is introduced at the piperazine ring formation step and 2-aminopyridyl substitution is incorporated via displacement. The resulting N,N' disubstituted piperazines act on the central nervous system at 5HT receptors.

12 Claims, No Drawings

PROCESS FOR SYNTHESIZING N-ARYL PIPERAZINES WITH CHIRAL N'-1-[BENZOYL(2-PYRIDYL)AMINO]-2-PROPANE SUBSTITUTION

This application claims priority from co-pending provisional application serial No. 60/363,431, filed on Mar. 12, 2002, the entire disclosure of which is hereby incorporated by reference.

FIELD OF THE INVENTION

This invention relates to the field of processes for synthesizing chiral substituted N-aryl piperazine compounds to provide compounds that bind to the 5HT receptors in the central nervous system and intermediates therefor.

BACKGROUND OF THE INVENTION

Some N,N' disubstituted piperazines, specifically those with N-aryl substitution, act on the central nervous system (e.g., bind to 5HT receptors). The *J. Med. Chem.* (1995), 38(20), 4044-55 and JP 61152655 teach the conventional approach to synthesize the aryl piperazine core, which involves reacting anilines with bis(dichloroethyl)amine. The resulting piperazines are elaborated by alkylating the resulting secondary amine.

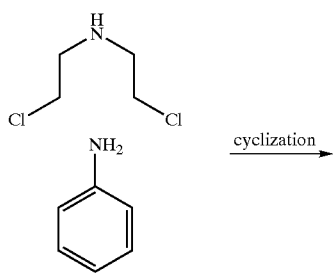

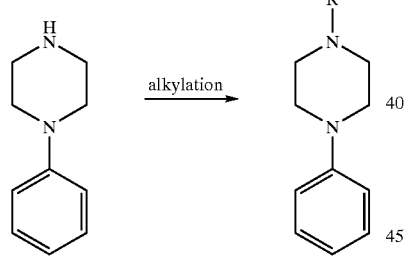

A "reversed" version of this chemistry is also possible. In this approach, an aniline mustard-like intermediate reacts with an alkyl amine, as shown, for example, in *J. Labeled Compounds and RadioPharm.* (1986) Vol XXIV, No. 4, 351. However, the commercial availability of bis(2-cholorethyl)amine hydrochloride relative to the general availability of aniline mustards makes this approach less attractive.

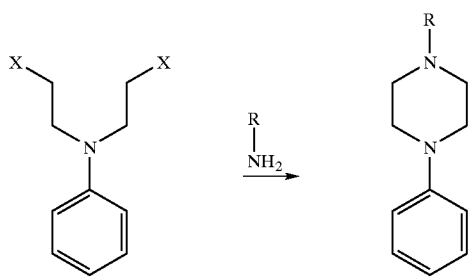

Asymmetric aryl piperazines are also formed by coupling piperazines with aryl triflates or bromides. *Tetrahedron Letters* (1998), 39, 2219 indicates that yields for this process are very (aryl) substrate dependent and generally are low.

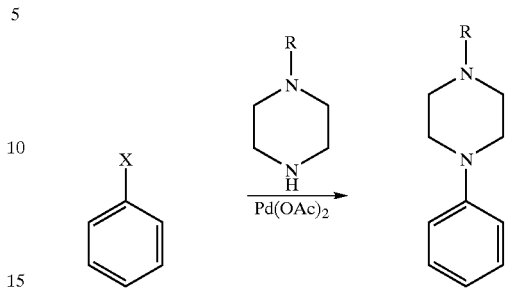

The formation of piperazines bearing a chiral center directly on nitrogen is the present invention's focus. Some methods for the formation of chiral N-piperazines are known. One known method is to resolve a racemic mixture, which has the disadvantage of wasting half the material.

Another known method is to displace a leaving group attached to a chiral center with an aryl piperazine. The barrier to displacement of the hindered leaving group is a problem, however. Enhancing the leaving group's reactivity creates other problems: JP 01125357 teaches that benzyl-(S)-bromopropionate reacts with 1-benzylpiperazine to give the expected (R) isomer displacement product. The carbonyl group, while activating the displacement process, also increases the susceptibility of the adjacent chiral center toward racemization under the reaction conditions.

WO 95/33743 reports an alternative that eliminates the racemization problem of activation by utilizing a chiral cyclic sulfamate as the reactive alkylating agent.

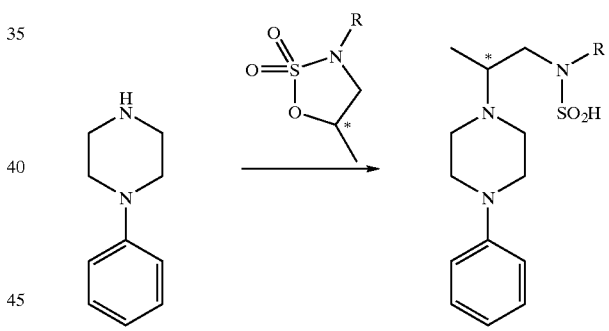

While cyclic sulfamates react readily with piperazines, the sulfamate itself requires numerous steps to prepare. In the case where R=2-pyridyl, for example, four separate chemical steps or transformations are required.

In *Acta Pol. Pharm.*, 56 (1), 41–47; 1999 it is reported that chiral amino acids reacting with N-methyl-N,N-bis(2-chloroethane). The carboxylic acid function makes the chiral center susceptible to racemization both during the reaction and during subsequent synthetic manipulations.

In another approach, *J. Med Chem.* 30(10), 1779-87; 1987 reports chiral benzyl amines react with a variety of mustards, both N-alkyl and N-aryl. The chiral amines employed were obtained by resolution.

WO94/24115 teaches the reaction of β-alkyl(and aryl)oxy chiral amines with mustards to form piperazine compounds.

To date, most syntheses of N-aryl N' substituted piperazines involve preforming the N-aryl piperazine followed by alkylation on N'. This approach is an efficient way to prepare many compound types. However, it is of limited practicality for the introduction of chirality α to the nitrogen because it relies on chiral alkylating agents that require multi-step syntheses to prepare.

SUMMARY OF THE INVENTION

The present invention comprises a process for preparing a compound of formula VII

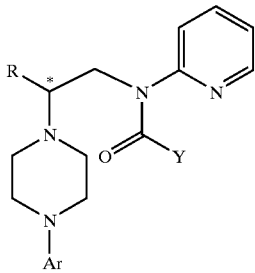

VII wherein

R is $C_1$–$C_3$ alkyl,

Y is $C_1$–$C_6$ alkoxy, $C_1$–$C_6$ alkyl, $C_3$–$C_7$ cycloalkyl or $C_3$–$C_7$ cycloalkoxy, and Ar is 2,3-dihydro-benzodioxin-5-yl, or phenyl optionally substituted with up to three substituents independently selected from halogen, methoxy, halomethyl, dihalomethyl and trihalomethyl, said process comprising:

a) reacting a compound of formula III with a chiral 2-amino-1-($C_3$–$C_5$)alkanol in a polar aprotic solvent to form a compound of formula IV

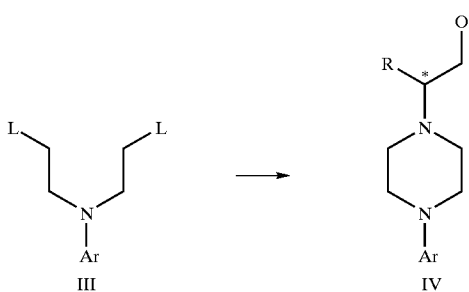

wherein L represents a leaving group selected from Cl, Br, mesylate and tosylate, and * indicates a chiral center;

b) converting the compound of formula IV to a compound of formula V

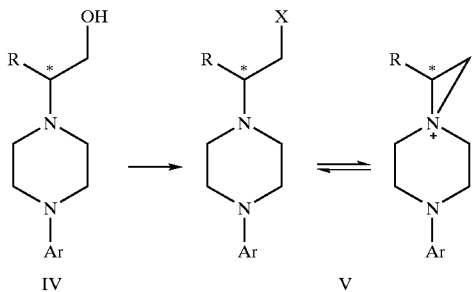

wherein X is Cl, Br, triflate, tosylate or mesylate; and, c) treating the compound of formula V with a compound of formula VI in an aprotic solvent

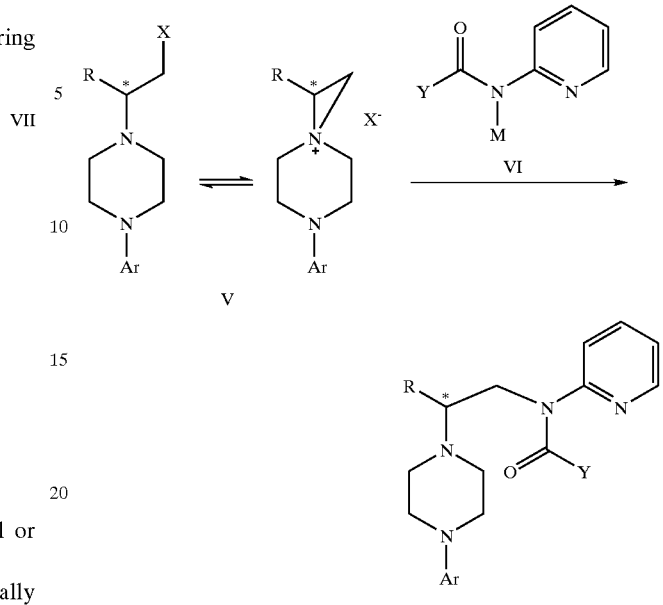

wherein M is an alkali metal (e.g., Na, Li, K) and Y represents a moiety selected from the group consisting of $C_1$–$C_6$ alkoxy, $C_1$–$C_6$ alkyl, $C_3$–$C_7$ cycloalkyl and $C_3$–$C_7$ cycloalkoxy.

This invention further comprises a process for making a compound of formula IX comprising steps (a), (b) and (c) above plus the steps of:

(d) treating the compound of formula VII with a protic acid to form a compound of formula VIII

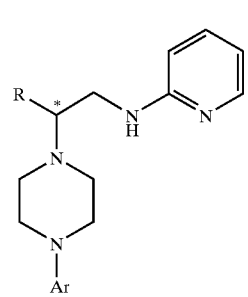

VIII and, (e) treating the compound of formula VIII with an aroyl compound selected from aroyl chloride, aroyl bromide and aroyl anhydride, in the presence of a base, to form a compound of formula IX

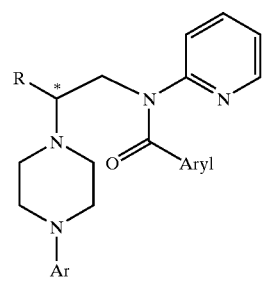

IX wherein Aryl represents a $C_6$–$C_{12}$ aromatic group optionally substituted with up to three substituents independently selected from the group consisting of halogen atoms, alkyl, alkoxy, alkoxycarbonyl, nitro, amino, alkylamino,

DETAILED DESCRIPTION OF THE INVENTION

A preferred embodiment of the present invention is a process for making N-aryl piperazines with chiral N'-1-[benzoyl(2-pyridyl)amino]-2-propane side-chains, which bind at the 5HT receptor. Another embodiment of this invention is a process for making intermediate compounds therefor. In the process of this invention, chirality is introduced at the piperazine ring formation step.

In a preferred embodiment of this invention, the synthesis begins with the creation of a dimesylate compound of formula III by first dialkylating an aniline of formula I with chloroethanol to form diol of formula II. Alternatively, the diol compound of formula II is prepared by dialkylation of the aniline with an alkyl haloacetate followed by reduction. The two hydroxyl groups are conveniently converted into suitable leaving groups, such as mesylate leaving groups:

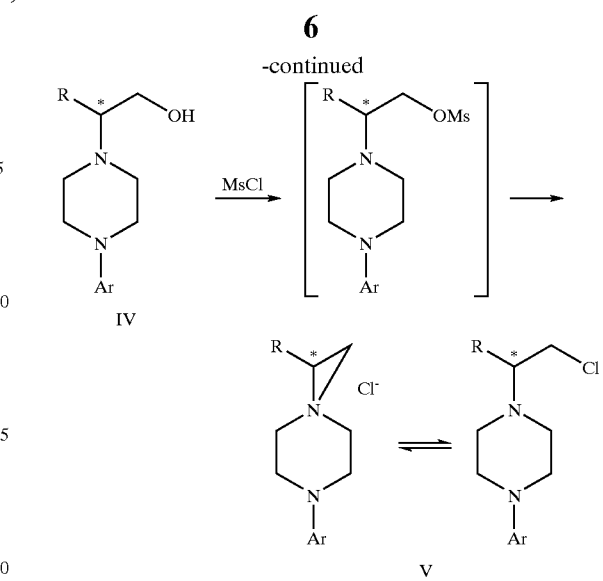

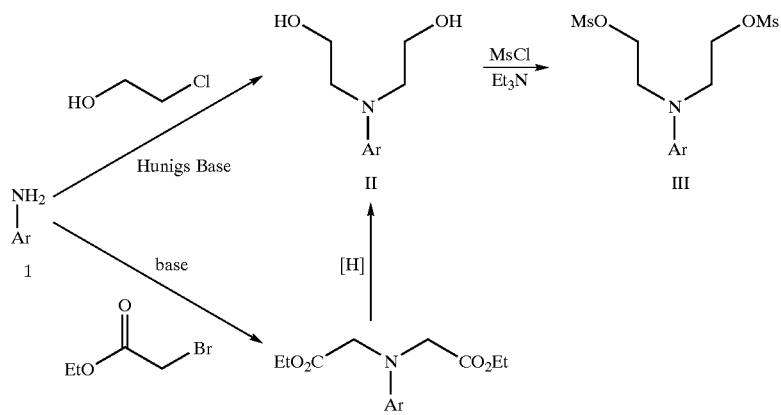

The dimesylate reacts with a chiral 2-amino-1-propanol (alaninol) to give the desired piperazine. In other embodiments of this invention, the chiral amino compound is 2-amino-1-butanol, 2-amino-1-pentanol, or 2-amino-3-methyl-1-butanol. Leaving groups other than mesylate may be used in the practice of this invention, including tosylate, chloro and bromo. The chirality of the amine component is preserved in the process. The alcohol group, which requires no protection during the cyclization, is poised for further structural elaboration. The resulting primary alcohol is then activated for displacement by, for example, treatment with methane sulfonyl chloride or bromide. This reaction is believed to form a mesylate which is a transient intermediate, and results in a compound of formula V.

In a preferred embodiment of this invention, the compound of formula V reacts with the anion derived from 2-(t-Boc)-aminopyridine to introduce an aminopyridyl side chain and produce a compound of formula VII.

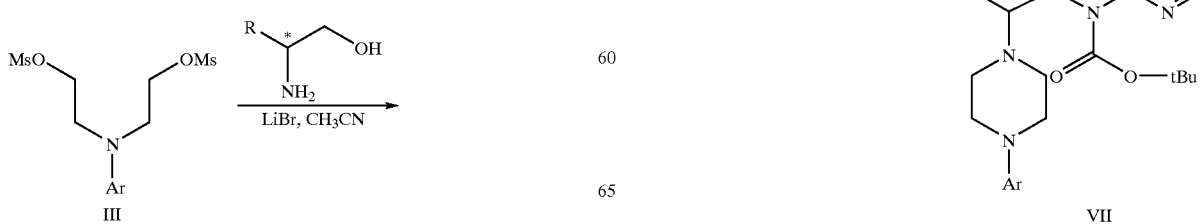

It is also within the scope of this invention to use other groups in place of the tert-butoxy group; suitable groups include $C_1$–$C_6$ alkoxy, $C_1$–$C_6$ alkyl, $C_3$–$C_7$ cycloalkyl and $C_3$–$C_7$ cycloalkoxy. Where this group is one of the aforesaid cyclic groups, one or more of the carbon atoms may be outside the cyclic ring, for example, cyclohexylmethoxy or ethylcyclopentyl.

The compound of formula VII can be further reacted to form compounds of formulae VIII and IX. Preferably, the t-Boc protecting group is removed with HCl/EtOH to form the amine of formula VII as an HCl salt. The salt can be used directly for functionalization of the free NH group. While the embodiment illustrated below indicates acylation with aroyl chlorides, other acyl derivatives may be used in the practice of this invention.

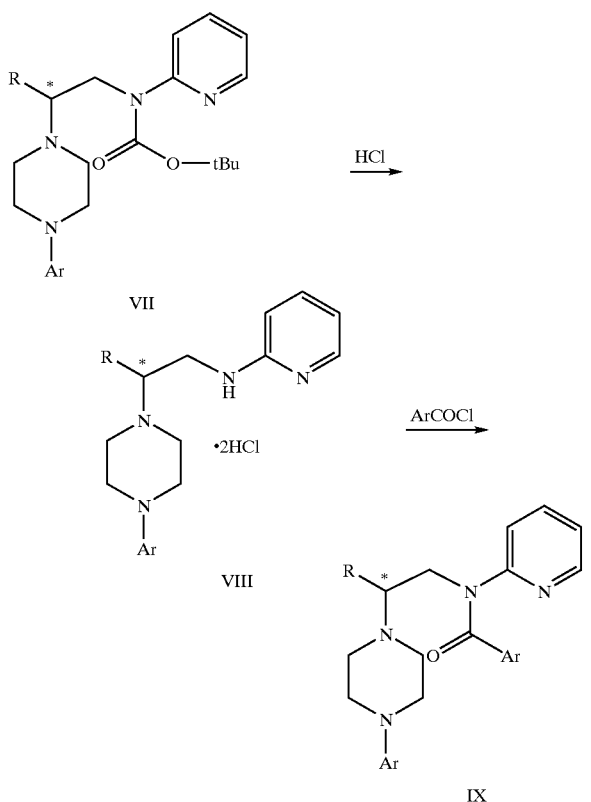

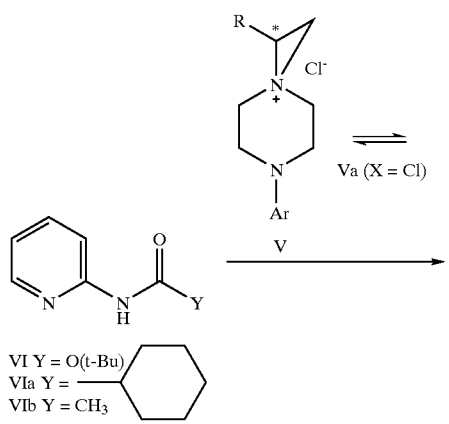

Since the present synthesis incorporates chirality during the piperazine forming step, a chiral amine is all that is required. The reaction is surprisingly very efficient even in the presence of a nearby free hydroxyl group (e.g., III IV).

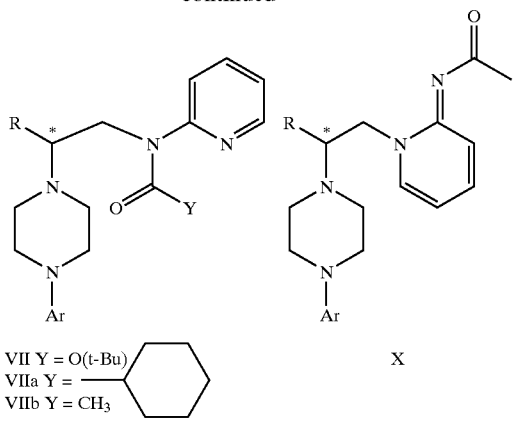

The hydroxyl group can then be used as a handle to introduce aminopyridyl functionality via displacement. It is not apparent on the surface or from the prior art how seriously the side reactions described above can threaten the usefulness of this displacement. Much depends on the specific alkylating reagent. In WO9703982, an aminopyridine VIa, under unspecified conditions, can be reacted with generic compounds Va, where X is a leaving group, to give VIIa. In the course of developing this invention, we observed that the anion of alkyl acyl compounds (i.e., VIb) when reacted with V (X=Cl) gave a significant quantity (ca. 20%) of undesired alkylation on the pyridyl nitrogen, forming compound X. In a preferred embodiment of the present invention, Y is an alkoxy group.

This invention provides a practical synthesis of N-aryl piperazines where chirality is introduced at the piperazine ring formation step and 2-aminopyridyl substitution is incorporated via displacement.

The use of t-Boc 2-amino pyridine, VI, as described in this invention significantly suppresses the amount (<7%) of analogous by-product formed, increasing the proportion of desired compound VII. As shown in the preceding section, the t-Boc protecting group is easily removed and the freed amine can then acylated.

Throughout this specification and in the appended claims, except where otherwise indicated, the terms halogen and halo refer to F, Cl and Br, and the terms alkyl, alkane, alkanol and alkoxy include both straight and branched chain alkyl groups.

The following examples are presented to illustrate certain embodiments of the present invention, but should not be construed as limiting the scope of this invention.

EXAMPLE 1

2-[(2,3-Dihydro-benzo[1,4]dioxin-5-yl)-(2-hydroxyethyl)-amino]-ethanol (II)

2,3-Dihydro-benzo[1,4]dioxin-5-ylamine (31.1 g, 0.2 mol) is mixed with 2-chloroethanol (210 mL, 3.1 mol) and Hunigs base (105 mL, 0.6 mol). The resulting dark solution is heated to 120° C. and stirred at this temperature with continuous monitoring by HPLC. After 12.5 h, the reaction is stopped. Ethyl acetate (300 mL) is added and the solution is washed with diluted brine (1×250 mL) followed by brine (2×75 mL). All aqueous layers are combined, the pH adjusted to 7 with $K_2CO_3$, and solution is back-washed with ethyl acetate (2×100 mL). All organic layers are then combined and extracted with 2N HCl (3×150 mL). The resulting aqueous solution is neutralized with solid $K_2CO_3$ to pH 7 and extracted with ethyl acetate (3×100 mL). The organic phase is dried with $MgSO_4$, concentrated and chased with toluene (2×50 mL) to remove residual chloroethanol. 39.6 g (80%) of crude product is obtained as a dark oil of 94 area % (LC-MS) purity. $^1H$ NMR ($CDCl_3$) δ6.88–6.70 (m, 3H), 4.34–4.22 (m, 4H), 3.54 (t, J=7.5 Hz, 4H), 3.18 (t, J=7.5 Hz, 4H).

EXAMPLE 2

Methanesulfonic Acid 2-[(2,3-dihydro-benzo[1,4] dioxin-5-yl)-(2-methanesulfonyloxy-ethyl)-amino]-ethyl ester (III)

To a solution of II (39.6 g, 0.165 mol) and triethyl amine (69 mL, 0.5 mol) in methylene chloride (250 mL), chilled to 5° C. in an ice-bath, is added a solution of mesyl chloride (38 mL, 0.5 mol) in methylene chloride (50 mL). The addition is carried out over 0.5 h at temperature not exceeding 18° C. The ice-bath is removed and resulting suspension is stirred at ambient temperature for 1 h. At that time, TLC and HPLC showed disappearance of starting material. The reaction mixture is washed with water (1×150 mL) and 5% aqueous $NaHCO_3$ solution (1×150 mL), dried with $MgSO_4$ and concentrated to afford III as red oil, crude yield 67.0 g (102%). $^1H$ NMR ($CDCl_3$) δ6.85 (m, 1H), 6.63 (m, 2H), 4.28 (m, 8H), 3.55 (t, J=7.5 Hz, 4H), 2.97 (s, 6H).

EXAMPLE 3

2-[4-(2,3-Dihydro-benzo[1,4]dioxin-5-yl)-piperazin-1-yl]-propan-1-ol (IV)

Dimesylate III (67.0 g, 0.17 mol), D-alaninol (14.0 g, 0.19 mol), lithium bromide (31.0 g, 0.35 mol), and potassium carbonate (74.8 g, 0.54 mol) are mixed together with acetonitrile (750 mL). The resulting suspension is refluxed (82° C.) for 27 h with monitoring by HPLC. The reaction mixture is cooled, filtered, and insoluble residue washed with acetonitrile. Mother liquor is concentrated to a small volume, filtered through 200 $cm^3$ of silica gel, and eluted with 1.5 L of MeOH 10% in EtOAc. After removing solvent on rotary evaporator, the residue is redissolved in EtOAc (200 mL). This solution is washed with water (2×50 mL), dried with $MgSO_4$ and concentrated to produce IV as thick golden oil that slowly crystallizes upon standing; yield 29.4 g (63%) and purity 88.3 area % (LC-MS). Melting point=91–92° C. $^1H$ NMR ($CDCl_3$) δ6.78 (t, J=7.5 Hz, 1H), 6.55 (m, 2H), 4.29 (m, 4H), 3.45 (dd, J=11, 5 Hz, 1H), 3.38 (t, J=11 Hz, 1H), 3.10 (br m, 4H), 2.86 (m, 3H), 2.63 (m, 2H), 0.96 (d, J=7.5 Hz, 3H).

EXAMPLE 4

6-(2,3-Dihydro-benzo[1,4]dioxin-5-yl)-1-methyl-6-aza-3-azoniaspiro[2.5]octane chloride (V)

Crude compound IV (29.4 g, 0.106 mol) and triethyl amine (16.2 mL, 0.116 mol) are dissolved in $CH_2Cl_2$ (150 mL) and to this solution is added a solution of mesyl chloride (8.6 mL, 0.111 mol) in $CH_2Cl_2$ (50 mL) under cooling at 5 to 15° C. over 0.5 h. Stirring is continued overnight at ambient temperature resulting in clear red solution. This solution is washed with water (1×100 mL) and 5% aq. $NaHCO_3$ (1×100 mL). Combined aqueous layers were back-washed with $CH_2Cl_2$ (2×50 mL). Organic layers are dried with $MgSO_4$ and concentrated to afford V as thick red oil, yield 31.6 g (101%). $^1H$ NMR ($CDCl_3$) δ6.76 (t, J=7.5 Hz, 1H), 6.55 (m, 2H), 4.27 (m, 4H), 4.11 (m, 1H), 3.10 (m, 4H), 2.8–2.64 (m, 5H), 2.54 (dd, J=7.5, 15 Hz, 1H), 1.55 (d, 3H).

EXAMPLE 5

{2-[4-(2,3-Dihydro-benzo[1,4]dioxin-5-yl)-piperazin-1-yl]-propyl}-pyridin-2-yl-carbamic acid tert-butyl ester (VII)

t-Boc-2-aminopyridine (24.7 g, 0.127 mol) and sodium t-butoxide (19.3 g, 0.2 mol) are mixed with THF (250 mL) and stirred for 0.5 h at RT. Chloride V (31.6 g, 0.106 mol) in THF (100 mL) is added to the mixture followed by solid $K_2CO_3$ (23.4 g, 0.17 mol). The reaction mixture is heated to reflux (68° C.). Stirred under reflux with monitoring by TLC (EtOAc/hexane 3:2, v/v). Starting material totally disappears after 97 h. The reaction mixture is cooled, diluted with EtOAc (400 mL), washed with water (3×150 mL) and brine (1×100 mL). Aqueous layers are back-extracted with EtOAc (2×75 mL). The combined organic solution is dried with $MgSO_4$ and concentrated to afford 49 g of crude oil containing (LC-MS) 67.9% of VII (yield-69%) and 10.8% of V. $^1H$ NMR ($CDCl_3$) δ8.35 (m, 1H), 7.66–7.45 (m, 2H), 7.00 (m, 1H), 6.75 (t, J=7.5H, 1H), 6.55 (br d, 1H), 6.4 (br d, 1H), 4.3–4.15 (m, 6H), 3.82 (dd, J=7, 14 Hz, 1H), 2.88 (m, 2H), 2.70 (m, 4H), 2.50 (m, 2H), 1.50 (s, 9H), 0.94 (d, J=7.5, 3H).

EXAMPLE 6

{2-[4-(2,3-Dihydro-benzo[1,4]dioxin-5-yl)-piperazin-1-yl]-propyl}-pyridin-2-yl-amine (VIII)

Compound VII as a crude oil (49.0 g, 0.106 mol) is dissolved in ethanol (150 mL) and to this solution is added 1N HCl solution in ethanol (212 mL). The resulting solution is refluxed for 18 h, then concentrated in vacuum to a small volume (~100 mL) until product starts to crystallize. Ether (100 mL) is added slowly to resulting slurry, in portions, and the mixture is stirred at ambient temperature for 2 h. Slightly gray crystals are filtered and washed with ethanol/ether (50:50) mixture to afford 22.2 g of compound VIII (49% over 3 steps). The purity is determined to be 97.9% by LC-MS. This batch is then recrystallized from methanol (150 mL) and ether (200 mL) to produce 19.3 g of VIII with 99% purity. $^1H$ NMR ($CD_3OD$) δ8.01 (m, 2H), 7.30 (d, J=9 Hz, 1H), 7.08 (t, J=7.4 Hz, 1H), 6.82 (t, J=8.1 Hz, 1H), 6.63 (m, 2H), 4.30 (m, 4H), 4.10 (m, 1H), 3.80–2.90 (m, 9H), 1.55 (d, J=6.2 Hz, 3H). MP=245–248° C.

EXAMPLE 7

4-Cyano-N-{2-[4-(2,3-dihydro-benzo[1,4]dioxin-5-yl)-piperazin-1-yl]-propyl}-N-pyridin-2-yl-benzamide (IXa)

Compound VIII (18.7 g, 0.044 mol) is added to a solution of $K_2CO_3$ (21.2 g, 0.15 mol) in 75 mL of water mixed with 90 mL of EtOAc at 0 to 5° C. The resulting 2-phase system was stirred for 0.5 h until all solids was dissolved. Then, solution of p-cyanobenzoyl chloride (8.0 g, 0.048 mol) in EtOAc (35 mL) was added over 15 min. at 5–7° C. The cooling bath was removed and the reaction mixture was stirred for 1 h at ambient temperature. The completion of reaction was established by TLC.

Organic layer was separated and washed with water (1×50 mL) and brine (1×50 mL). Combined aqueous layers were back-washed with EtOAc (1×60 mL). Combined EtOAc solution was dried with $MgSO_4$ and filtered then refluxed for 0.5 h with charcoal Darco (2 g) and filtered through Celite. The mother liquor was diluted with heptane (90 mL) and slurried for 2 h with silica gel (20 g). After filtering silica gel off, filtrate was concentrated to afford free base of IXa as thick oil with LC purity 94.5%.

This oil was dissolved in EtOAc (100 mL) and treated with 37 mL of 1.2N HCl solution in EtOAc at 20–25° C. Hydrochloride precipitated as white solid, was collected by filtration and dried under vacuum at 50° C. to afford IX with yield 20.8 g (91% for this step, 19.4% over 7 steps from I). $^1H$ NMR ($CD_3OD$) δ8.59 (m, 1H), 7.72 (m, 1H), 7.66 (d, J=8.3 Hz, 2H), 7.53 (d, J=8.3 Hz, 2H), 7.36 (m, 1H), 7.03 (d, J=8.3 Hz, 1H), 6.83 (m, 1H), 6.66 (m, 2H), 4.52 (m, 1H), 4.30 (m, 5H), 3.90 (m, 1H), 3.72 (m, 4H), 3.61 (m, 4H), 3.45 (m, 1H), 3.20 (m, 2H), 1.50 (d, J=7 Hz, 3H).

EXAMPLE 8
Alkylation of Benzodioxane Aniline to Diester

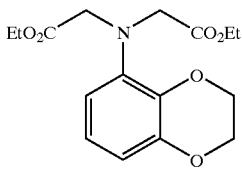

A mixture of benzodioxane aniline (3.0 g, 20 mmol), ethyl bromoacetate (7.5 mL, 68 mmol), Hunig's base (12.5 mL, 72 mmol) and NaI (0.3 g, 2.0 mmol) in toluene (30 mL) was heated to reflux. After 23 h, the reaction mixture was cooled to rt. Water (25 mL) was added. The two layers were separated. The aqueous layer was extracted with toluene (25 mL). The combined organic layers were dried over $Na_2SO_4$, filtered and concentrated in vacuo to give 6.5 g (100%) yield of the diester as brown oil. $^1$H NMR ($CDCl_3$) δ6.70 (t, J=8.1 Hz, 1H), 6.3–6.6 (m, 2H), 4.1–4.3 (m, 12H), 1.2–1.3 (m, 6H).

EXAMPLE 9
Reduction of Benzodioxane Diester to Diol

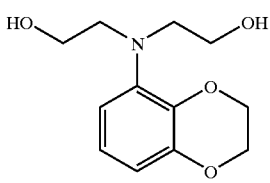

IV

A mixture of diester (24 g, 74.3 mmol) in THF (240 mL) was cooled to 0–5° C. before LAH pallets (9.9 g, 260 mmol) were added slowly while maintaining reaction temperature below 10° C. After the addition of LAH, the cooling bath was removed and stirring was continued at rt overnight. After 18 h of stirring, the reaction mixture was cooled to 0±5° C. in dry ice/IPA bath. Water (10 mL) was added to reaction mixture slowly, followed by 15% aq. sodium hydroxide (10 mL) and water (30 mL). The resulted mixture was stirred for 30 min then filtered. The solids were washed with THF (100 ml). The filtrate was concentrated in vacuo to give 14.5 g (81%) of diol of formula IV as thick clear oil of 98 area % (LC-MS) purity. $^1$H NMR ($CDCl_3$) δ6.88-6.70 (m, 3H), 4.34–4.22 (m, 4H), 3.54 (t, J=7.5 Hz, 4H), 3.18 (t, J=7.5 Hz, 4H).

Many variations of the present invention not illustrated herein will occur to those skilled in the art. The present invention is not limited to the embodiments illustrate and described herein, but encompasses all the subject matter within the scope of the appended claims and equivalents thereof.

What is claimed is:

1. A process for preparing a compound of formula VII

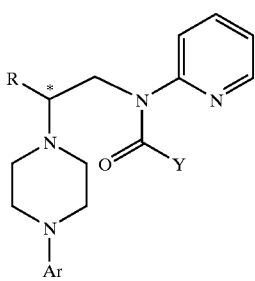

VII wherein
R is $C_1$–$C_3$ alkyl,
Y represents a moiety selected from the group consisting of $C_1$–$C_6$ alkoxy, $C_1$–$C_6$ alkyl, $C_3$–$C_7$ cycloalkyl and $C_3$–$C_7$ cycloalkoxy, and Ar is 2,3-dihydro-benzodioxin-5-yl, or phenyl optionally substituted with up to three substituents independently selected from halogen, methoxy, halomethyl, dihalomethyl and trihalomethyl, said process comprising the following steps:
a) reacting a compound of formula III with a chiral 2-amino-1-($C_3$–$C_5$)alkanol in a polar aprotic solvent to form a compound of formula IV

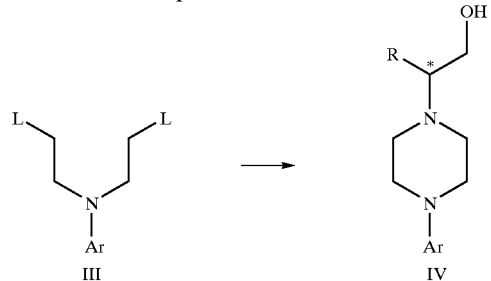

wherein L represents a leaving group selected from the group consisting of Cl, Br, mesylate, triflate and tosylate, and * indicates a chiral center;

b) converting the compound of formula IV to a compound of formula V

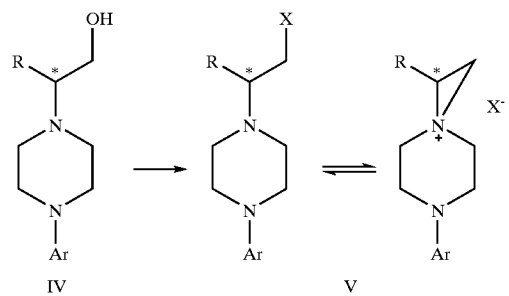

wherein X is Cl or Br; and, c) treating the compound of formula V with a compound of formula VI in an aprotic solvent

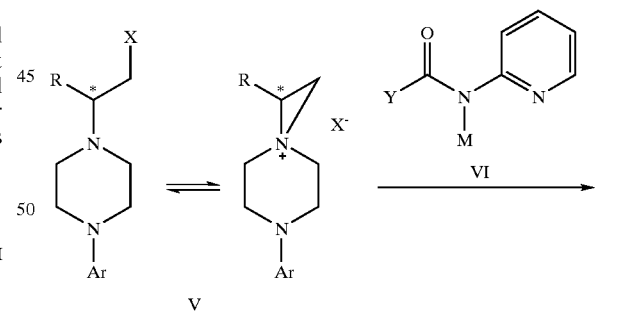

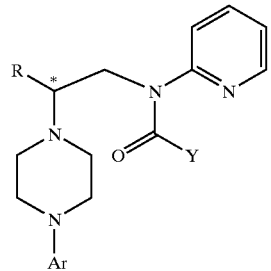

VII wherein M is an alkali metal.

2. A process according to claim 1 further comprising treating the compound of formula VII with a protic acid to form a compound of formula VIII

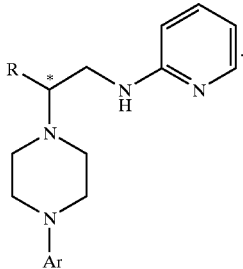

VIII

3. A process according to claim 2 further comprising treating the compound of formula VIII with an aroyl chloride, aroyl bromide or aroyl anhydride in the presence of a base to form a compound of formula IX

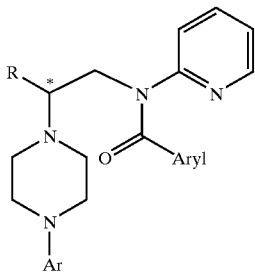

IX wherein Aryl represents a $C_6$–$C_{12}$ aromatic group optionally substituted with up to three substituents independently selected from the group consisting of halogen atoms, alkyl, alkoxy, alkoxycarbonyl, nitro, amino, alkylamino, dialkylamino, haloalkyl, dihaloalkyl, trihaloalkyl, nitrile and amido substituents each having no more than six carbon atoms.

4. A process according to claim 3 wherein Aryl is 4-cyanophenyl.

5. A process according to claim 3 wherein the compound of formula III is formed by
   a) reacting a compound of formula I with a 2-chloroethanol in the presence of a trialkylamine base to form a compound of formula II

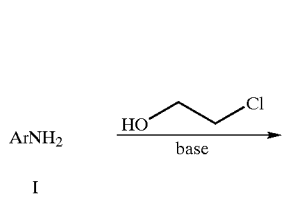

and,
   b) converting the compound of formula II to the compound of formula III.

6. A process according to claim 1 wherein the compound of formula III is formed by
   a) reacting a compound of formula I with 2-chloroethanol in the presence of a trialkylamine base to form a compound of formula II

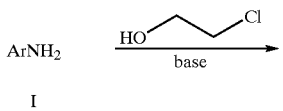

and,
   b) converting the compound of formula II to the compound of formula III.

7. A process according to claim 1 wherein Y is a $C_1$–$C_6$ alkoxy group.

8. A process according to claim 1 wherein Y is tert-butoxy.

9. A process according to claim 1 wherein Ar is 2,3-dihydro-benzodioxin-5-yl.

10. A process according to claim 1 wherein the chiral 2-amino-1-($C_3$–$C_5$)alkanol is D-2-amino-1-propanol and R is methyl.

11. A process according to claim 1 wherein: Y is tert-butoxy; Ar is 2,3-dihydro-benzodioxin-5-yl; the chiral 2-amino-1-($C_3$–$C_5$)alkanol is D-2-amino-1-propanol; and R is methyl.

12. A process according to claim 11 further comprising treating the compound of formula VII with a protic acid to form a compound of formula VIII

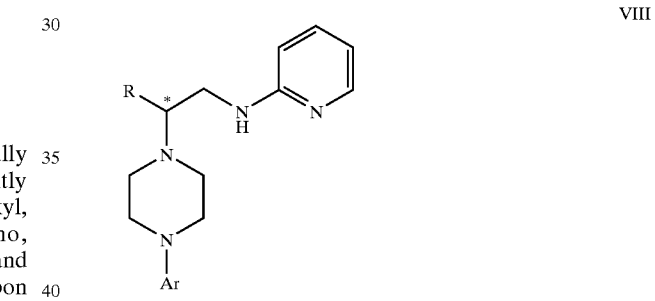

VIII and comprising treating the compound of formula VIII with an aroyl chloride, aroyl bromide or aroyl anhydride in the presence of a base to form a compound of formula IX

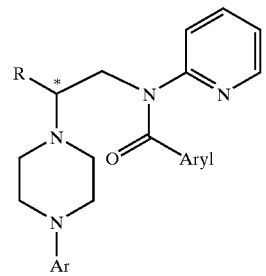

IX wherein Aryl represents phenyl optionally substituted with up to three substituents independently selected from the group consisting of halogen atoms, alkyl, alkoxy, alkoxycarbonyl, nitro, amino, alkylamino, dialkylamino, haloalkyl, dihaloalkyl, trihaloalkyl, nitrile and amido substituents each having no more than six carbon atoms.

* * * * *